United States Patent [19]

Hu et al.

[11] Patent Number: 5,378,636
[45] Date of Patent: Jan. 3, 1995

[54] GEMINAL DIPHENYL DERIVATIVES AND THEIR USE IN IMMUNOASSAYS

[75] Inventors: Mae W.-L. Hu, Los Altos; Kirk Schulkamp; Cheng-I Lin, both of San Jose; Edwin F. Ullman, Atherton, all of Calif.

[73] Assignee: Syntex (U.S.A.) Inc., Palo Alto, Calif.

[21] Appl. No.: 105,834

[22] Filed: Aug. 12, 1993

Related U.S. Application Data

[62] Division of Ser. No. 755,203, Sep. 4, 1991, Pat. No. 5,256,575, which is a division of Ser. No. 289,998, Dec. 22, 1988, Pat. No. 5,063,165.

[51] Int. Cl.⁶ .................. G01N 33/78; G01N 33/531
[52] U.S. Cl. ................................ 436/500; 436/501; 436/825
[58] Field of Search ............... 436/500, 501, 825; 562/44; 560/55

[56] References Cited

U.S. PATENT DOCUMENTS

| | | | |
|---|---|---|---|
| 3,911,096 | 10/1975 | Chopra . | |
| 3,928,553 | 12/1975 | Hollander . | |
| 4,173,464 | 11/1979 | Noguchi et al. | 543/259 |
| 4,208,205 | 6/1980 | Fawzi | 504/337 |
| 4,263,039 | 4/1981 | Noguchi et al. | 504/287 |
| 4,435,332 | 3/1984 | Noguchi et al. | 558/392 |
| 4,468,469 | 8/1984 | Atkinson | 435/7.7 |
| 4,602,946 | 7/1986 | Nagubandi . | |
| 4,622,293 | 11/1986 | Ellis et al. | 436/804 |
| 4,632,697 | 12/1986 | Nagubandi . | |
| 5,024,691 | 6/1991 | Nagubandi . | |
| 5,063,165 | 11/1991 | Hu et al. | 436/500 |
| 5,256,575 | 10/1993 | Hu et al. | 436/501 |

FOREIGN PATENT DOCUMENTS

0133464A1 2/1985 European Pat. Off. .

OTHER PUBLICATIONS

Tillman, et al., CLINCA CHIMICA ACTA, vol. 161 (1986), pp. 233-238 "Effect of Fenoprofen on Thyroid Function Tests".
Huckle et al (1981) Drug Metab. Dispos. 9(4):352-9.
Izumi et al. (1984) Nippon Noyaku Gakkaishi 9(2):259-67.
Crayford et al (1980) Xenobiotica 10(5):355-364.
Hutson et al (1987) Pestic. Sci 12:12:385-398.
Battista et al. (1985) J. Chromatogr. 345:77-89.
Bopp et al (1981) J. Pharm. Sci. 70(5):507-509.

Primary Examiner—Kay K. A. Kim
Attorney, Agent, or Firm—Theodore J. Leitereg; Janet K. Kaku

[57] ABSTRACT

Methods are disclosed for inactivating interfering binding proteins in a immunoassay for a member of a specific binding pair (sbp). The method comprises including in an assay medium containing a sample suspected of containing an sbp member and an interfering binding protein an effective amount of a water soluble compound having two substituted or unsubstituted phenyl groups linked to a common atom. When the sbp member or its sbp partner has two phenyl groups linked to a common atom, the compound has a number of groups other than hydrogen attached to the phenyl groups and the atom that differs by at least two from the number of such groups on the sbp member. When the sbp member or its sbp partner has two phenyl groups linked to a common atom and the binding protein is not an antibody, the compound has only one group other than hydrogen attached to a phenyl group or the common atom. The methods have particular application in avoiding cross-reactivity of non-analyte materials in a sample with immunochemical reagents used in such assay. The methods have application also in disrupting complexes between an analyte to be determined and other materials so that one can accurately determine the amount of an analyte in a sample.

7 Claims, No Drawings

GEMINAL DIPHENYL DERIVATIVES AND THEIR USE IN IMMUNOASSAYS

This is a divisional of application Ser. No. 07/755,203, filed Sep. 4, 1991, now U.S. Pat. No. 5,256,575, which in turn is a divisional of Ser. No. 289,998 filed Dec. 22, 1988, now U.S. Pat. No. 5,063,165 which issued on Nov. 5, 1991.

BACKGROUND OF THE INVENTION

1. Field of the Invention

The invention relates generally to the field of receptor binding assays for analytes in samples suspected of containing the analyte. One problem associated with receptor binding assays for analytes is that samples containing the analytes may contain other materials that will bind receptor reagents utilized in an assay. For example, the interfering material can bind to an antibody which is utilized in the assay, thus reducing the amount of antibody available for binding to an analyte. Another problem is that some analytes bind to interfering materials present in the sample and become complexed. In a complex form the analyte is unavailable for binding to receptors used in the assay and therefore an accurate assay for such analyte is difficult to achieve. Consequently, it becomes necessary to disrupt the binding of the analyte with the interfering material prior to or simultaneously with conducting the assay for the analyte without disrupting binding of the analyte to the receptor.

Urine samples from individuals taking certain non-steroidal, anti-inflammatory drugs such as fenoprofen contain a substance that cross reacts with a subset of the polyclonal antibodies used in testing for drugs of abuse such as antibodies to tetrahydrocannabinol, benzodiazapine, or phenobarbital. The cross-reactive substance or substances are metabolities of fenoprofen that are believed to have little structural resemblance with the analytes to be determined. In order to achieve a more specific assay, it is important that the binding of the cross-reactive antibodies to the interfering metabolites be substantially reduced or eliminated.

Samples to be assayed for the presence of triiodothyronine and tetraiodothyronine also contain thyroxine binding globulin (TBG) which binds to the triiodothyronine or tetraiodothyronine. As a result, quantitation of such analytes in untreated samples is not possible with an immunoassay because a number of molecules of the material free from complexation with TBG will vary with the TBG concentration of the sample. Consequently, it is necessary to disrupt the binding of the triiodothyronine or tetraiodothyronine with TBG prior to or simultaneously with conducting an assay without interfering with binding of the analyte with antibody used in the assay. One compound that has been utilized to displace triiodothyronine and tetraiodothyronine from TBG is 8-anilinonaphthalene-1-sulfonic acid.

2. Description Of The Related Art

The use of anilinonaphthalene sulfonic acid for displacing tetraiodothyronine from TBG in assays for tetraiodothyronine is described in U.S. Pat. Nos. 3,928,553 and 3,911,096. European Patent Application 0,133,464 describes the use of 2-hydroxy-4-methoxybenzophenone-5-sulfonic acid and its salts as thyroxine binding protein blocking agents for use in immunoassays and also refers to U.S. patent application Ser. No. 414,934 filed Sep. 3, 1982, as disclosing substituted phenylacetic acids.

SUMMARY OF THE INVENTION

One aspect of the present invention concerns methods for inactivating interfering binding proteins in an immunoassay for an sbp member such as a ligand without interfering with the binding of the sbp member with its receptor, such as an antibody. Another aspect of the invention concerns methods for essentially completely disrupting complex formation between a ligand and a binding protein. The methods comprise including in a medium containing a ligand an effective amount of a water soluble compound having a structure comprised of two substituted or unsubstituted phenyl groups linked to a common atom wherein the structure may be further substituted. When the ligand has two phenyl groups linked to a common atom, the compound utilized in the method of the invention has a number of groups other than hydrogen attached to the phenyl groups and the atom that differs from the number of such groups on the ligand by at least two. When the ligand has two phenyl groups linked to a common atom and the binding protein is not an antibody, the compound has only one group other than hydrogen attached to a phenyl group or the common atom.

Compounds useful in the method of the invention have the following formula:

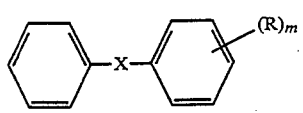

wherein:

X is selected from the group consisting of O, NH, P, N, C, S, and CH$_2$ wherein the unsatisfied valencies of N, C, P, and S can be satisfied by single or double bonds to O, S, or C atoms which are parts of groups having molecular weights of from 14 to 200, such groups being comprised of hydrogen, carbon, nitrogen, oxygen and sulfur;

R groups are independently groups of 1 to 12 atoms other than hydrogen which may include a chain of 1–10 atoms other than hydrogen or can be taken together, or taken with X, to form a non-benzenoid ring having three to eight atoms other than hydrogen, which atoms referred to in all of the above are independently selected from the group consisting of halogen, carbon, nitrogen, oxygen, phosphorous and sulfur wherein at least one R contains a water solubility imparting moiety; and m is a number between 1 and 12, with the proviso that when the ligand has two phenyl groups linked to a common atom, the compound utilized in the method of the invention has a number of groups other than hydrogen attached to the phenyl groups and the atom that differs from the number of such groups on the ligand by at least two and when the ligand has two phenyl groups linked to a common atom and the binding protein is not an antibody, the compound has only one group other than hydrogen attached to a phenyl group or the common atom.

Another aspect of the invention concerns a method for reducing interference by fenoprofen and its metabolites in an analyte binding assay. The method comprises contacting the binding protein used in assaying a sample suspected of containing the analyte with an effective amount of one of the aforementioned compounds.

Another aspect of the present invention concerns a method for releasing thyroid hormones from thyroid binding globulin in a sample to be analyzed without interfering with binding of thyroid hormones to antibodies used in the assay. Such method comprises contacting a sample to be analyzed with an effective amount of one of the compounds mentioned above.

The invention further includes certain N-(3-phenoxybenzoyl)amino acid derivatives, compositions comprising such derivatives, and kits for conducting an assay.

DESCRIPTION OF THE SPECIFIC EMBODIMENTS

One aspect of the present invention concerns compounds useful to prevent binding of an analyte to a first class of binding proteins in an assay so as to permit binding of the analyte to a second class of binding proteins employed as an assay reagent where the first class of binding proteins is present in the analytical sample or is a subset of the second class of binding proteins, usually antibodies, that is cross-reactive with the analyte and interfering substances. A requirement is, therefore, that the compound does not bind competitively with analyte to the antibody population required for the assay.

As mentioned above, another aspect of the present invention concerns methods for essentially completely disrupting complex formation between a ligand and a binding protein. The methods comprise including in a medium containing a ligand and a binding protein an effective amount of water soluble compound having a structure comprised of two substituted or unsubstituted phenyl groups linked to a common atom wherein the structure may be further substituted. When the ligand has two phenyl groups linked to a common atom, the compound useful in the invention has a number of groups other than hydrogen attached to the phenyl groups and the common atom which number differs from the number of such groups on the ligand by at least two. When the ligand analyte has two phenyl groups linked to a common atom and the binding protein is not an antibody, the compound has only one group other than hydrogen attached to a phenyl group or to the common atom.

By the term "essentially completely disrupting complex formation" is meant that the compound of the invention either prevents substantial binding between the ligand and a binding protein or, where a complex is already formed between the ligand and a binding protein, the compound of the present invention acts in such a way as to render the ligand substantially free of complexation with the binding protein. The binding protein will be a subset of all the binding proteins present in the medium. In both situations usually at least 80% of the interfering binding protein will be prevented from binding the ligand, frequently 90 percent, preferably at least 99%.

By the term "substituted" is meant that a C, N, P, or S atom of the structure

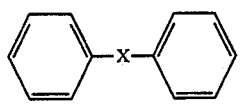

is bound to a group other than hydrogen. The exact nature of such group will be evident from the description below. Conversely, by the term "unsubstituted" is meant that the atom has no substituent or is bound to hydrogen. The groups or substituents may include as part thereof alkyl, including lower alkyl and alkyl of 6 to 20 C atoms, hydroxy, —O—, —S—, COOH, SO₃H, OPO₃H₂, C=O, =O, CONH, NH₂, —NH—, SH, halo, NO₂, CN, aryl, heterocyclic groups, etc.

Before proceeding further with a description of the present invention, a number of terms will be defined.

Ligand—any organic compound for which a binding protein naturally exists or can be prepared. The ligand can be analyte or a compound present in a sample containing the analyte that interferes with detection of the analyte.

Analyte—a compound or composition to be measured that is capable of binding specifically to a binding protein, usually an antigen such as a drug; a member of a specific binding pair.

The precise nature of drug analytes together with numerous examples thereof are disclosed in U.S. Pat. No. 4,299,916 to Litman, et al., particularly columns 16 to 23, and in U.S. Pat. No. 4,275,149, columns 17 and 18, the disclosures of which are incorporated herein by reference.

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular or ring members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narcine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, such as the cannabinoids which include cannabinol and tetrahydrocannabinol.

The next group of drugs includes the vitamins such as A, B, e.g., $B_{12}$, C, D, E and K, folic acid, and thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, lidocaine, procaineamide, acetylprocaineamide, propranolol, griseofulvin, valproic acid, butyrophenones, antihistamines, anticholinergic drugs, such as atropine, their metabolites and derivatives.

The next group of drugs is the tricyclic antidepressants including derivatives of dibenzazepine, dibenzocycloheptadiene, and dibenzoxepin such as amitriptyline, nortriptyline, imipramine, disipramine, protriptylene, trimipramine, chlomipramine, and doxepin.

Metabolites related to disease states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

The invention has particular application to cannabinoids, methaqualone, benzodiazepines, barbiturates, phenytoin, thyronines, tricyclic antidepressants, and the like.

Member of a specific binding pair ("sbp member")—one of two different molecules having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormone-hormone receptor, nucleic acid duplexes, IgG-protein A, DNA-DNA, DNA-RNA, and the like are not immunological pairs but are included in the definition.

Binding Protein—any compound or composition capable of recognizing a particular spatial and polar organization of a molecule, e.g., epitopic or determinant site. Illustrative binding proteins include naturally occurring receptors, e.g., thyroxine binding globulin, antibodies, enzymes, Fab fragments, lectins, and the like. When several related binding proteins are used such as subsets of polyclonal antibodies, the binding protein may be one such subset.

Antibody—an immunoglobulin, or derivative or fragment thereof, having an area on the surface or in a cavity which specifically binds to and is thereby defined as complementary with a particular spatial and polar organization of another molecule. The antibody can be monoclonal or polyclonal and can be prepared by techniques that are well known in the art such as, for example, immunization of a host and collection of sera or hybrid cell line technology.

Antibody for the analyte—an antibody specific for an analyte.

The method of the invention has application where the ligand analyte has the formula:

$$[A](R_1)_q$$

wherein:

A is a group having the structure E(D) where E is a substituted or unsubstituted 6-membered ring such as phenyl, pyridyl, piperidyl, pyranyl, cyclohexyl, etc.; D is a substituted or unsubstituted benzene ring bound to E through a bond or through an atom selected from the group consisting of oxygen (O), sulfur (S), nitrogen (N), phosphorous (P) or carbon (C);

$R_1$ is each independently selected from the group consisting of a chain of 1–10 atoms other than hydrogen consisting of halogen, carbon, nitrogen, oxygen, and sulfur and are substituents on A connected by single or double bonds, or can be taken together to form a ring; and q is 1 to 6.

In one particular aspect a ligand has the formula:

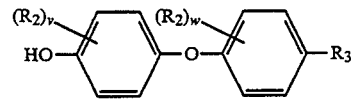

wherein:

$R_2$ in the above formula is independently selected from the group consisting of hydrogen, halogen, including bromine, chlorine, iodine, and lower alkyl of from 1 to 4 carbon atoms, including methyl, ethyl, isopropyl, and tert-butyl;

$R_3$ in the above formula is a group that consists of from one to ten atoms other than hydrogen, which atoms are independently selected from the group consisting of one or more of carbon, oxygen and nitrogen. The group may contain a carboxylic acid, ester, or amide functionality; and v and w are independently 0 to 2.

Illustrative compounds are 3', 3", 5'-triiodothyronine, and 3', 3", 5', 5"-tetraiodothyronine.

As mentioned above, other analytes of special interest are cannabinoids, methaqualone, benzodiazepines, barbiturates, phenytoin, thyronines, and tricyclic antidepressants.

Compounds useful in the methods of the present invention are preferably water soluble and have the following formula:

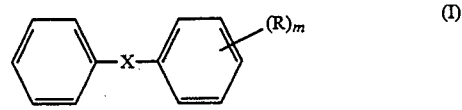

(I)

wherein:

X is selected from the group consisting of O, NH, P, N, C, S, and $CH_2$ wherein the unsatisfied valencies of N, C, P and S can be satisfied by single or double bonds to O, S, or C atoms which are parts of groups having molecular weights of 14 to 200 comprised of hydrogen, carbon and nitrogen; in one embodiment both hydrogens on a carbon atom may be replaced by a double bond to O, C or N or by single bonds to one atom of a ring having three to eight atoms other than hydrogen, which atoms are independently selected from the group consisting of carbon, nitrogen, oxygen and sulfur;

R groups are independently groups of 1 to 12 atoms other than hydrogen which may include a chain of 1–10 atoms other than hydrogen or can be taken together with each other or with X to form a non-benzenoid ring having five to eight atoms other than hydrogen, which atoms referred to in all of the above are independently selected from the group consisting of halogen, carbon, nitrogen, oxygen, phosphorous and sulfur wherein at least one R contains a water solubility imparting moiety; and m is a number between 1 and 12, with the proviso that when the ligand has two phenyl groups linked to a common atom, the compound utilized in the method of the invention has a number of groups other than hydrogen attached to the phenyl groups and the common atom that differs from the number of such groups on the ligand by at least two and when the ligand has two phenyl groups linked to a common atom and the class of binding protein is not an antibody, the compound has only one group other than hydrogen attached to a phenyl group or the common atom.

Preferred compounds for use in the methods of the present invention have the following formula:

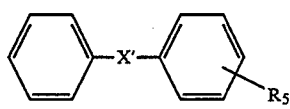

(I)

wherein:

X' in the above formula is selected from the group consisting of O, NR$_4$, S(O)$_y$, C=O, and C(R$_4$)$_2$, wherein y is a number from 0 to 2 and R$_4$ is independently selected from the group consisting of hydrogen and lower alkyl or wherein, alternatively, R$_4$ can be taken together to form a ring having five to eight atoms other than hydrogen, which atoms are independently selected from the group consisting of carbon, nitrogen, oxygen, and sulfur. The ring may contain, by way of example and not limitation, —CONHCONH—, —CH$_2$CH$_2$CH$_2$CH(COOH)—, —OCH$_2$CH$_2$O—, —(CH$_2$)$_4$—, —(CH$_2$)$_2$NH(CH$_2$)$_2$—;

R$_5$ in the above formula is a group of from one to twelve atoms, preferably three to twelve atoms, other than hydrogen, which atoms are independently selected from the group consisting of carbon, nitrogen, oxygen, phosphorus and sulfur; preferably, R$_5$ includes a water solubility imparting moiety. A group or functionality imparting water solubility is a hydrophilic functionality which renders the compound soluble in water to an extent of at least one micromolar. Such functional group or functionality can include a sulfonate, phosphate, phosphonate, carboxylate, hydroxyl, amine, ether, amide, and the like. Illustrative R$_5$ groups are carboxyalkyl, sulfonoxyalkyl, CONHOCH$_2$COOH, CO-NH (glucose), SO$_2$NHCH$_2$COOH, SO$_3$H, CONHCH$_2$CH$_2$SO$_3$H, PO$_3$H$_2$, OPO$_3$H$_2$, hydroxyl, carboxyl, ketone, and combinations thereof.

As mentioned above, when the ligand has two phenyl groups linked through an atom, the compound has a number of groups other than hydrogen attached to the phenyl groups and the atom. This number differs from the number of such groups on the ligand by at least two. For example, the analyte in an assay may be diphenylhydantoin, which has the structure:

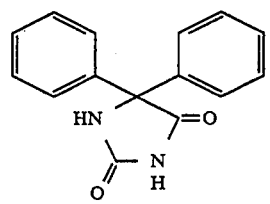

A metabolite of diphenylhydantoin which may cross react in an assay has the structure:

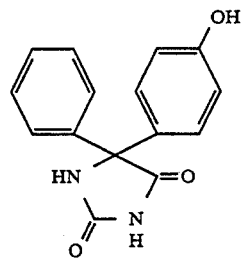

Accordingly, compounds used in accordance with the present invention for essentially completely disrupting complex formation between the metabolite and a subset of antibodies that bind to the metabolite and to diphenylhydantoin would be compounds of formula I such as:

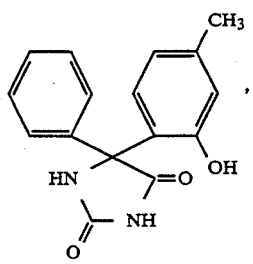

COMPOUND IA

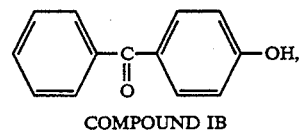

COMPOUND IB

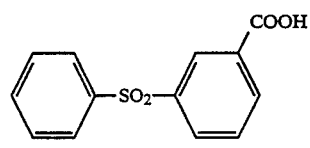

COMPOUND IC

As can be seen, compound IA has two groups, namely, —CH$_3$ and —OH, on a phenyl group whereas the ligand diphenylhydantoin has hydrogens in the corresponding positions. Compound IB has an oxygen on the atom joining the phenyl groups and an OH on the phenyl ring whereas diphenylhydantoin has a five-membered ring on the atom joining the phenyl groups and a hydrogen in the corresponding position on a phenyl ring. Compound IC differs from diphenylhydantoin in having a sulfur as a linking atom with two oxygens and a carboxyl group on a phenyl ring.

Further, as mentioned above, when the ligand has two phenyl groups linked to a common atom and the first binding protein is not an antibody, the compound has only one group other than hydrogen attached to a phenyl group or the common atom. For example, for a thyronine analyte in serum, thyroxine binding globulin (TBG) is present and binds thyronine, thus increasing the potential for an inaccurate assay. TBG is a binding protein but is not an antibody. Therefore, a compound for inactivating TBG in an assay for a thyronine analyte might be, for example, compound IIIG or IIIH (infra), which have only one group other than hydrogen attached to a phenyl group or the common atom.

Preferred compounds for use in the methods of the present invention have the formula:

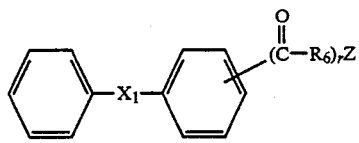

wherein:

$R_6$ in the above formula is $TN(R_7)W$ wherein T and W are independently a bond or linear or branched chains comprised of 1 to 4 carbon atoms and 0 to 1 oxygen atoms. The linear or branched chain may include a non-oxocarbonyl group, which may be found, for example, in an ester or amide functionality. $R_7$ in the above formula is H, $CH_3$ or $CH_2CH_3$ and r is zero or 1.

Z in the above formula is COOH, $SO_3H$, or $PO_3H_2$; and $X_1$ is O, $NR_8$, C=O, $S(O)_t$, $C(R_8)_2$ wherein $R_8$ is independently selected from the group consisting of hydrogen and lower alkyl and t is zero to 2.

Particularly preferred compounds for use in the methods of the present invention are the following: IIIA wherein r is zero, $X_1$ is O and Z is COOH; IIIB wherein r is 1, T is a bond, $R_7$ is H, W is $CH_2CH_2$, Z is $SO_3H$, and $X_1$ is $CH_2$; IIIC wherein r is 1, T is a bond, $R_7$ is $CH_3$, W is $CH_2$, Z is COOH, and $X_1$ is O; IIID wherein r is 1, T is a bond, $R_7$ is H, W is $CH_2$, Z is COOH, and $X_1$ is O; IIIE wherein r is 1, T is a bond, $R_7$ is H, W is $CH(CH_3)$, Z is COOH, and $X_1$ is O; IIIF wherein r is 1, T is a bond, $R_7$ is H, W is $OCH_2$, Z is COOH, and $X_1$ is O; IIIG wherein r is 1, T is a bond, $R_7$ is H, W is $CH_2CH_2$, Z is $SO_3H$, and $X_1$ is 0; and IIIH wherein r is 1, T is a bond, $R_7$ is H, W is $CH_2CH_2$, Z is COOH, and $X_1$ is 0.

The compounds useful in the methods of the present invention can be prepared according to the following general procedure:

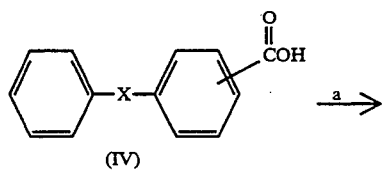

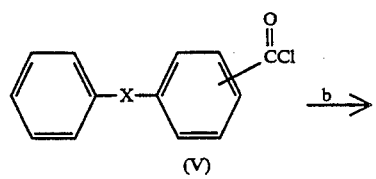

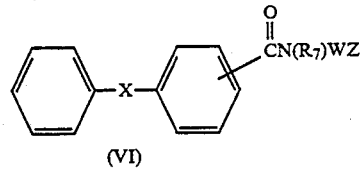

wherein X, $R_7$, W, and Z are as defined above; a involves formation of an acid chloride by treatment with, for example, thionyl chloride, oxalylchloride, or phosphorous oxychloride, under conventional conditions; and b involves treatment of an acid chloride with $H_2N(R_7)W$-Z under conditions for nitrogen displacement of chloride to form an amide linkage, such as methanol and triethyl amine, or the like.

Compound IV where X is 0 is commercially available. Compound IV where X is C=O may be prepared by a procedure similar to that described in *J. Org. Chem.* (1985) 50(16): 2093-2904

Compound IV where X is S may be prepared by a procedure similar to that described in Ger. Offen. DE 2619489 (1976).

Compound IV where X is $SO_2$ may be prepared by a procedure similar to that described in Ger. Offen. DE 2252014 (1973)

Compound IV where X is NH is discussed in *Org. Mass Spectrom.* (1984) 19(9): 438-441

In carrying out the methods of the invention an aqueous medium will normally be employed. Other polar solvents may also be employed, usually oxygenated organic solvents of from 1-6, more usually from 1-4 carbon atoms, including alcohols, ethers and the like. Usually these cosolvents will be present in less than about 40 weight percent, more usually in less than about 20 weight percent.

The pH for the medium will usually be in the range of about 4-11, more usually in the range of about 5-10, and preferably in the range of about 5.4-9.5. The pH is chosen so as to maintain a significant level of disruption of binding between a ligand and a binding protein while optimizing binding between an analyte and its complementary binding protein. In some instances, a compromise will be made between these two considerations. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the methods and usually constant temperatures during the period of the methods. The temperatures for the determination will generally range from about 10°-50° C., more usually from about 15°-40° C.

An effective amount of a compound used in accordance with the invention to essentially completely disrupt complex formation between a ligand and a binding protein is at least 1 μM and will generally vary from about 10 μM to 10 mM, more usually from about 100 to 1000 μM.

Where the present method is used in conjunction with an assay, considerations such as whether the assay is qualitative, semi-quantitative or quantitative, the particular detection technique, and the concentration of the analyte will normally determine the concentration of the other reagents. While the concentrations of the various reagents will generally be determined by the concentration range of interest of the analyte, the final concentration of each of the reagents will normally be determined empirically to optimize the sensitivity of the assay over the range of interest. The total binding sites of the members of the specific binding pair which are complementary to the analyte will be not less than about 0.1 times the minimum concentration of interest based on binding sites of the analyte and not more than about 10,000 times the maximum concentration of interest based on analyte binding sites, usually about 0.1–1000 times, more usually about 0.3–10 times, the maximum concentration of interest. For ligand analyte, where labelled ligand is employed, the concentration range of the labelled ligand based on equivalents will generally be not less than about $10^{-6}$, more usually not less than $10^{-2}$, times the minimum concentration of interest and not greater than 100, usually not greater than 10, times the maximum concentration of interest.

The order of addition of the various reagents may also vary and is dependent on what type of assay is utilized wherein many of the same considerations mentioned above apply.

The present method has application both to hetereogeneous and homogenous assays. Exemplary heterogeneous assays are found in U.S. Pat. Nos. 4,256,834 and 4,261,968. Homogeneous immunoassays are exemplified by immunofluorescence methods such as those disclosed in U.S. Pat. No. 3,993,345, enzyme channeling techniques such as those disclosed in U.S. Pat. No. 4,233,402, and other enzyme immunoassays as discussed in Maggio, supra, and in U.S. Pat. No. 3,817,837. The assay can be competitive or direct and can involve compounds of the invention that are either labeled ligand or labeled receptor.

A particular embodiment of the invention concerns a method for reducing interference by fenoprofen and its metabolites in an analyte binding assay. The method comprises contacting the antibody used in assaying a sample suspected of containing the analyte with an effective amount of a compound of the formula:

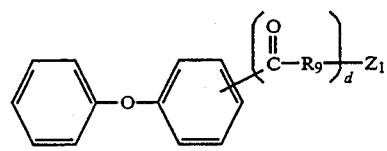

III wherein:

$R_9$ is $T_1N(R_{10})W_1$ wherein $T_1$ and $W_1$ are independently a bond or linear or branched chains comprised of 1 to 4 carbon atoms and 0 to 1 oxygen atoms and $R_{10}$ is H or lower alkyl of from 1 to 5 carbon atoms, d is 0 or 1, and $Z_1$ is COOH, $SO_3H$, or $PO_3H_2$.

Another embodiment of a method in accordance with the present invention is a method for releasing thyroid hormones such as triiodothyronine and tetraiodiothyronine from thyroid binding globulin in a sample to be analyzed. The method comprises contacting said sample with an effective amount of compound III.

A particular aspect of the present invention includes a compound of the formula:

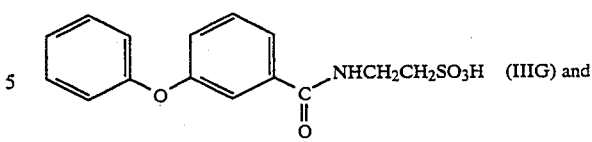

a compound of the formula:

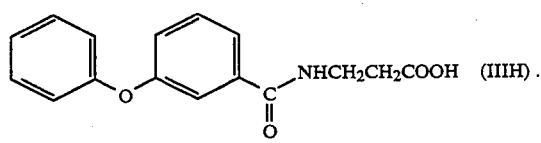

Also included within the scope of the invention are compositions comprising a sample to be analyzed and a compound of the invention such as IIIG or the compound IIIH.

As a matter of convenience, the reagents employed in the present invention can be provided in a kit in packaged combination in predetermined amounts. The reagents can be separately contained or two or more reagents can be combined in a single container depending on their stability and cross-reactivity. For use in assaying for an analyte in a sample, the reagents may include a compound of the invention as disclosed above, and, where appropriate, conjugates of signal generating compounds and specific binding pair members or other reaction partners to provide the detectable signal. In addition, other additives such as ancillary reagents may be included. The relative amounts of the various reagents may be varied widely, to provide for concentractions in solution of the reagents which substantially optimize the sensitivity of an assay. The reagents can be provided as dry powders, usually lyophilized, including excipients, which on dissolution will provide for a reagent solution having the appropriate concentrations for performing an assay.

EXAMPLES

The invention is further demonstrated by the following illustrative examples. Parts and percentages are by weight to volume unless otherwise indicated.

EXAMPLE 1

Preparation of m-(phenoxy)benzoylchoride

In a well ventilated hood, a mixture of m-phenoxy benzoic acid (200 g, 0.933 mole) (Aldrich) and thionyl chloride (105 mL, 1.44 moles) was placed in a one liter, round-bottomed flask. The flask was fitted with a magnetic stirring bar (or mechanical stirring bar for larger quantity preparation) and a reflux condenser with calcium chloride drying tube, which was attached to an exit tube, for evolved hydrogen chloride and sulfur dioxide, leading to a gas absorption trap. The mixture was heated on a heating mantle cautiously at first until a brownish-green solution was obtained (about 1½ hours). The resulting solution was then heated gently for an additional 1½ hours. The resulting brown solution was then cooled, and excessive thionyl chloride was distilled off at 40° C. To the resulting oil was added toluene (75 mL), and the solution was evaporated to remove a small amount of thionyl chloride. Addition and evaporation of toluene (75 mL) was repeated once more. The resulting acid chloride was then dissolved in 100 mL of tetrahydrofuran (THF dried over molecular sieves 3A), and ready to use freshly for reaction.

EXAMPLE 2

Preparation of N-(m-phenoxybenzoyl) tauric acid (PBTA)

A solution of taurine (116 g, 0.927 mole) in a mixture of solution containing tetrahydrofuran (300 mL), 40% sodium hydroxide (43.5 mL) and water (940 mL) was placed in a three-necked, round-bottomed flask (3 liters). The reaction flask was fitted to a pH meter and equipped with two addition funnels. The m-phenoxybenzoyl chloride (prepared in Example 1) in THF solution was added slowly, through the addition funnel protected from moisture using calcium chloride drying tube, to the taurine solution (pH adjusted to 8.9 before reaction) at room temperature. Simultaneously, a solution of 40% sodium hydroxide (total of 155 mL) was added slowly through the second addition funnel to adjust the pH of the reaction between 8.5 and 9. The addition took 5 to 7 hours. The resulting yellow solution was allowed to stand at room temperature overnight. Complete reaction was observed on thin layer chromatography (tlc).

The product was then acidified using concentrated HCl (about 4.5 mL) to pH 2.5, and the aqueous solution was extracted using ether (20×100 mL) until the complete removal of starting material (monitored by tlc, silica gel plate, 0.1:2:8:acetic acid:$CH_3OH$:$CH_2Cl_2$). To the resulting solution (about 1.4 liters) was slowly stirred in powdered sodium chloride (50 grams) until sodium chloride dissolved completely, and the solution was mixed with 1 liter of 35% sodium chloride solution. The crude product (about 360 g) thus obtained was recrystallized in 1.4 liters of 1:1/MeOH:9% NaCl. The resulting white crystals were collected by suction and dried overnight. The suctioned dried crystals were transferred to a vacuum desiccator and dried at room temperature for 48 hours or until constant weight. The product (267 g, one spot on tlc, Rf 0.68, butanol:methanol:benzene:water/2:1.25:1:1, silica gel plate) showed nmr ($D_2O$) peaks at 3.04 ppm (t, 2H), 3.63 ppm (t, 2H), 6.89 ppm–7.39 ppm (m, 9H) and UV λ max. at 278 nm.

EXAMPLE 3

The purpose of this experiment was to study the effects of PBTA as a dissociating agent for measuring thyroxine (T4) in a sample population. An Emit ® (Syva Company, Palo Alto, Calif. ACA ® T4 assay (E. I. DuPont de Nemours Company, Wilmington, Del. was used as a model system for this experiment.

Materials

The antibody reagent contains antibodies from sheep immunized with a protein-T4 conjugate, stabilizers and preservatives in a 0.055M Tris solution (pH 6.0). Enzyme reagent contains a T4 analog chemically coupled to glucose-6-phosphate dehydrogenase, stabilizers and preservatives in a 0.055M Tris solution (pH 7.0). PBTA was formulated in a 0.1M Tris buffer (pH 9.0) with preservatives at 5, 10 and 20 mg/mL concentrations. For purposes of comparison, 8-anilinonaphthalenesulfonic acid (ANS, a recognized T4 dissociating agent) was formulated in a 0.1M Tris buffer at 3 mg/mL.

The ACA T4 assay pack configuration was as follows:

Dimple 1—Serum treatment
Dimple 2—Buffer tab
Dimple 3—G6P/NAD tab
Dimple 4—Antibody reagent
Dimple 5—Empty
Dimple 6—Enzyme reagent
Dimple 7—Empty Each pack was self contained for one sample determination. The volume of antibody, enzyme and serum treatment (PBTA or ANS) was 60 μL each for all tests.

Protocol

For each pack run, ACA instrument injected 200 μL of calibrator or sample and 4800 μL of water into the pack. The pack was then preheated to 37° C. during a 100 second incubation. The first four dimples were then opened and mixed with the diluted sample. After a four minute incubation, the last three dimples were opened and mixed in with the sample. Absorbance readings were started 30 seconds later for a kinetic rate determination. Optical measurements were taken for 17 seconds. All operations of the ACA were handled automatically and were set by the manufacturer.

Results

The rates and quantitations are summarized in Table 1. Reference data on the samples were obtained independently by a different methodology (Clinical Assays Total $T_4$ Radioimmunoassay (RIA)) to assess any differences between the serum treatments. All quantitation data was generated using a log-logit equation to generate a standard curve from the calibrator rates and assigned concentrations.

Scattergrams and linear regression statistics were generated to fully assess the differences, if any, between the serum treatment reagents. The results are summarized in Table 1.

TABLE 1

| Additive | Reagent[1] conc. (mg/mL) | Final[2] conc. (mM/L) | Assay range[3] | % Modulation[4] | Corr Coeff. | SEE[5] |
|---|---|---|---|---|---|---|
| PBTA | — | — | 260 | 37.5 | .950 | 1.142 |
| PBTA | 5 | 0.186 | 300 | 35.5 | .958 | 1.170 |
| PBTA | 10 | 0.374 | 360 | 38.8 | .977 | 0.759 |
| PBTA | 20 | 0.748 | 354 | 36.7 | .982 | 0.694 |
| ANS | 3 | 0.120 | 342 | 38.3 | .968 | 0.823 |

[1]Reagent conc. = Additive concentration in the serum treatment reagent
[2]Final conc. = Additive concentration in the final reaction mixture
[3]Assay range = Rate of #5 calibrator minimus rate of #1 calibrators
[4]% Modulation = $\frac{(\#5 \text{ cal rate minimus } \#1 \text{ cal rate}) \times 100}{\#5 \text{ cal rate}}$
[5]SEE = Standard error of the estimate.
cal = calibrator

Discussion

It is clear from the data in the table that the serum treatments have an effect on the assay. The rates from the standard curves increase along with the increasing concentration of PBTA. This indicates that PBTA is affecting the ability of serum proteins to bind to T4. This effect can also be seen on the scattergrams. The data points on the scattergrams fit in a tighter distribution about the linear regression line with higher PBTA concentrations. Notice that above the threshold concentration of 5 mg/mL PBTA the Standard Error of the Estimate (SEE) drops indicating that sample to sample differences on binding proteins is being overcome. ANS is widely used as a T4 dissociating agent and when used in this assay configuration produced comparable data as evidenced by the similarity of SEE and correlation statistics.

EXAMPLE 4

The purpose of this experiment was to study the effects of PBTA on reducing the interference of derivatives of fenoprofen in an EMIT ® assay for benzodiazepines in urine. The fenoprofen derivatives are found in urine of individuals taking fenoprofen.

The antibody reagent contained antibodies from sheep immunized with a protein-diazepam conjugate, stabilizers and preservatives in a 55 mM Tris solution, pH 5.2, and glucose-6-phosphate (G6P)(66 mM) and nicotine adenine dinucleotide (NAD+)(40 mM)(EMIT ® benzodiazepine assay, Reagent A, Syva Company) with PBTA at 0.5 mg/ml. The enzyme reagent contained a diazepam analogue chemically coupled to glucose-6-phosphate dehydrogenase (G6PDH), stabilizers and preservatives in a 55 mM Tris solution (pH 8.0) (EMIT ® benzodiazepine assay, Reagent B, Syva Company). The assay buffer solution contained 0.5% NaCl, surfactant and preservatives in 55 mM Tris (pH 8.0). For comparison, the reagents were compared to reagents prepared and optimized without PBTA.

For each test, 50 μL sample, 50 μL antibody reagent, 50 μL enzyme reagent, and 750 μL assay buffer were combined and aspirated into a Gilford Stasar III flow cell at 30° C. After a delay of 15 seconds, absorbance measurements were made for 30 seconds (two per second) at a wavelength of 340 nm. A rate measurement was made by calculating the linear regression of the absorbance measurements for the 30 seconds and multiplying the subsequent rate by 2.667.

The rates for benzodiazepine calibrators using reagents with PBTA (X02) and without PBTA (W01) are shown in Table II. Rates from samples from individuals taking fenoprofen are shown relative to the value of the 300 ng/mL calibrator (+/−rate). All samples were confirmed to be negative for benzodiazepines by gas chromatography/mass spectrometry (GC/MS). The data show that the presence of the assay system to the analogues of fenoprofen present in the urine samples.

TABLE II

| REAGENTS | X02 | W01 |
|---|---|---|
| CALIBRATOR | | |
| NEGATIVE | 359 | 329 |
| 300 ng/ml | 445 | 416 |
| 500 ng/ml | 466 | 448 |
| 1000 ng/ml | 500 | 502 |
| SAMPLES | | |
| F102R | −20 | +6 |
| F019R | −44 | −9 |
| F017R | −58 | −16 |
| F088R | −45 | +4 |
| F103Z | −48 | −1 |
| F021R | −46 | −1 |
| F104Z | −59 | −6 |
| F-BQ | −46 | +7 |

Derivatives prepared below were as follow:

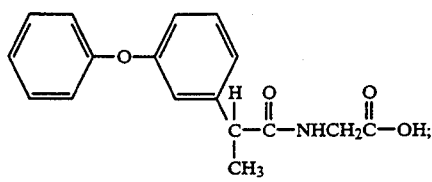

(1) glycyl fenoprofen

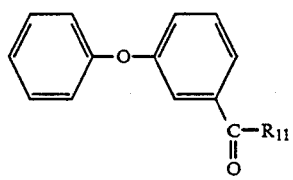

(2) $R_{11} = NHCH_2CH_2—\overset{O}{\underset{\|}{C}}—OH$ β-alanine (3) $R_{11} = NHCH_2\overset{O}{\underset{\|}{C}}—OH$ glycine (4) $R_{11} = N(CH_3)CH_2—\overset{O}{\underset{\|}{C}}—OH$ sarcosine (5) $R_{11} = NHCH_2CH_2CH_2SO_3H$ (6) $R_{11} = NH_2OCH_2CO_2H$ (7) $R_{11} = NHCH_2\overset{O}{\underset{\|}{C}}—NHCH_2\overset{O}{\underset{\|}{C}}—NHCH_2\overset{O}{\underset{\|}{C}}—OH$

EXAMPLE 5

Preparation of N-hydroxysuccinimic ester of m-phenoxybenzoic acid

To a solution of m-phenoxybenzoic acid (2.0 g, 9.3 mmoles) in tetrahydrofuran (25 ml, freshly distilled) was added 1,3-dicyclohexylcarbodiimide (3.2 g, 15.5 mmoles) and N-hydroxysuccinimide (1.2 g, 10 mmoles). The resulting mixture was allowed to stir at room temperature under nitrogen for 18 hours, and the formation of N-hydroxysuccinimic ester of m-phenoxybenzoic acid was observed. The resulting N-hydroxysuccinimic ester was then used freshly for reaction.

EXAMPLE 6

Preparation of m-phenoxybenzoylamidopropanesulfonic acid (5)

To a mixture of 3-amino-1-propanesulfonic acid (488 mg, 3.5 mmoles), triethylamine (354 mg, 3.5 mmoles) and THF (2 ml) was added a solution of N-hydroxysuccinimic ester of m-phenoxybenzoic acid (from 500 mg of m-phenoxybenzoic acid in 6.5 ml of tetrahydrofuran described in Example 5). The resulting reaction mixture was then allowed to stir at room temperature. After 18 hours, the reaction product was acidified to pH3 and then extracted using dichloromethane to remove starting material. The resulting aqueous solution was then evaporated to dryness and to the residue was added methanol and the suspension was filtered. The filtrate thus obtained was then chromatographed on silica gel plate (20% MeOH/CH$_2$Cl$_2$) and the product was eluted using the same solvent to yield 100 mg of m-phenoxybenzoylamidopropanesulfonic acid.

EXAMPLE 7

Preparation of m-phenoxybenzoylamido-oxy-acetic acid (6)

The preparation of m-phenoxybenzoylamido-oxy-acetic acid (6) was carried out using a procedure similar to that for m-phenoxybenzoylamidopropanesulfonic acid described in Examples 5 and 6.

EXAMPLE 8

Preparation of m-phenoxybenzoyl glycyl glycyl glycine (7)

The preparation of m-phenoxybenzoyl glycyl glycyl glycine (7) was carried out using a procedure similar to that for m-phenoxybenzoylamidopropanesulfonic acid described in Examples 5 and 6.

EXAMPLE 9

Preparation of m-phenoxybenzoyl β-alanine (2)

The preparation of m-phenoxybenzoyl β-alanine (2) was carried out using a procedure similar to that for N-(m-phenoxybenzoyl)tauric acid (PBTA) described in Example 2.

EXAMPLE 10

Preparation of m-phenoxybenzoyl glycine (3)

The preparation of m-phenoxybenzoyl glycine (3) was carried out using a procedure similar to that for N-(m-phenoxybenzoyl)tauric acid (PBTA) described in Example 2.

EXAMPLE 11

Preparation of m-phenoxybenzoyl sarcosine (4)

The preparation of m-phenoxybenzoyl sarcosine (4) was carried out using a procedure similar to that for N-(m-phenoxybenzoyl)tauric acid (PBTA) described in Example 2.

EXAMPLE 12

Preparation of glycyl fenoprofen (1)

A mixture of fenoprofen (130 mg, 0.53 mmole), 1,3-dicyclohexylcarbodiimide (120 mg, 0.58 mmole), N-hydroxysuccinimide (67 mg, 0.58 mmole) in tetrahydrofuran (3 ml, freshly distilled) was allowed to stir at room temperature overnight. The resulting N-hydroxysuccinimic ester of fenoprofen was then added into a solution of glycine (450 mg, 6 mmoles) in sodium bicarbonate solution (0.05M, pH 8.6, 3 ml) with the adjustment of pH at 8.6. The resulting product was then acidified to pH 3 and extracted with ethyl acetate. The organic solvent was evaporated and the product was chromatographed on silica gel plates (butanol:methanol:benzene:water/2:1.25:1:1) and eluted using the same solvents. The solvent was then evaporated and to the residue was added 10% MeOH/CH$_2$Cl$_2$ and filtered. The filtrate was evaporated to dryness to yield glycyl fenoprofen (1).

The invention has been described in detail with particular reference to the above embodinents. It will be understood, however, that variations and modifications can be effected within the spirit and scope of the invention.

What is claimed is:

1. A composition for use in an assay for a member of a specific binding pair (sbp), said composition comprising an assay medium comprising (a) a sample suspected of containing said sbp member, and (b) a compound of the formula:

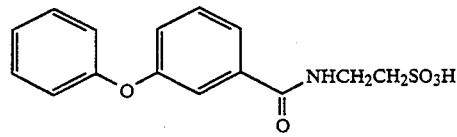

2. The composition of claim 1 for use in inactivating an interfering binding antibody which may be present in said sample.

3. The composition of claim 1 for use in inactivating thyroxine binding globulin which may be present in said sample.

4. The composition of claim 1 for use in reducing interference by fenoprofen and its metabolites in said assay.

5. A composition for releasing thyroid hormones from thyroid binding globulin in a sample to be analyzed, said composition comprising a sample and an effective amount of a compound of the formula:

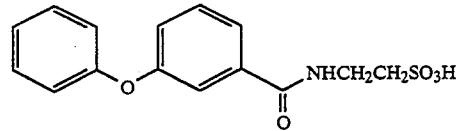

6. A composition of claim 5 wherein said thyroid hormones are selected from triiodothyronine or tetraiodothyronine.

7. A kit for conducting an assay for an analyte, comprising in packaged combination (a) a compound of the formula:

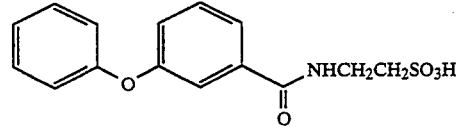

and (b) reagents for conducting said assay wherein said reagents include an antibody capable of binding said analyte but not said compound.

* * * * *